(12) United States Patent
Xie et al.

(10) Patent No.: US 7,947,747 B2
(45) Date of Patent: May 24, 2011

(54) JOINT PROCESS FOR PREPARING ALCOHOL/ETHER MIXTURES ALCOHOL/HYDROCARBON MIXTURES, AND SYNTHESIZING AMMONIA

(76) Inventors: Dingzhong Xie, Changsha (CN); Fengyu Dai, Changsha (CN); Yong Feng, Changsha (CN); Chunyang Li, Changsha (CN)

( * ) Notice: Subject to any disclaimer, the term of this patent is extended or adjusted under 35 U.S.C. 154(b) by 1096 days.

(21) Appl. No.: 10/546,288

(22) PCT Filed: Feb. 19, 2003

(86) PCT No.: PCT/CN03/00136
§ 371 (c)(1),
(2), (4) Date: Mar. 23, 2007

(87) PCT Pub. No.: WO2004/074226
PCT Pub. Date: Sep. 2, 2004

(65) Prior Publication Data
US 2007/0161716 A1 Jul. 12, 2007

(51) Int. Cl.
*C07C 27/00* (2006.01)
(52) U.S. Cl. .......... 518/715; 518/713; 518/717; 518/719
(58) Field of Classification Search .................. 518/713, 518/715, 717, 719
See application file for complete search history.

(56) References Cited

FOREIGN PATENT DOCUMENTS

| | | |
|---|---|---|
| CN | 90105545 | 7/1991 |
| CN | 1 117 942 A | 3/1996 |
| CN | 93105920.8 | 2/1997 |
| CN | 1 412 169 A | 4/2003 |
| EP | 0081948 A1 | 6/1983 |

OTHER PUBLICATIONS

Chemical Fertilizer Design, vol. 40, No. 5, Oct. 25, 2002, Dingzhong Xie, pp. 18-21.

*Primary Examiner* — Jafar Parsa
(74) *Attorney, Agent, or Firm* — Birch, Stewart, Kolasch & Birch, LLP

(57) ABSTRACT

A joint process for preparing alcohol/ether mixtures, alcohol/hydrocarbon mixtures and synthesizing ammonia is disclosed. In particular, a process of converting CO and $CO_2$ present in the feed gas of ammonia synthesis, comprising $H_2$ and $N_2$ as major components, into useful co-products is disclosed. The process is characterized in that the alcohol/ether forming reaction is firstly carried out by using a copper series catalyst, then the alcohol/hydrocarbon forming reaction is carried out by using an iron series catalyst, the individually formed alcohol/ether and alcohol/hydrocarbon products are separated by water cooling and condensing, and discharged into corresponding storage tanks, and the remaining gas, in which the amount of CO and $CO_2$ is less than or equal to 10 ppm, is fed into the ammonia synthesis system. Since the alcohol/hydrocarbon can be used as liquid fuel, the product composition of the ammonia plant is improved, and the amount of $CH_4$ fed into the ammonia synthesis system is decreased, and the amount of venting is thus reduced.

10 Claims, 2 Drawing Sheets

US 7,947,747 B2

JOINT PROCESS FOR PREPARING ALCOHOL/ETHER MIXTURES ALCOHOL/HYDROCARBON MIXTURES, AND SYNTHESIZING AMMONIA

RELATED APPLICATIONS

This application is the national stage of International Application PCT/CN2003/000136, filed in China on Feb. 19, 2003.

FIELD OF THE INVENTION

The present invention relates to a process for preparing alcohol/ether mixtures, alcohol/hydrocarbon mixtures, and synthetic ammonia, is used for chemical production, and belongs to the chemical field.

BACKGROUND OF THE INVENTION

It is well known that the feed gas for ammonia synthesis must be clean $H_2$ and $N_2$ during the production of an ammonia plant. But the content of $H_2$ and $N_2$ is from 91% to 97%, and that of CO and $CO_2$ is from 1% to 8% in general feed gas, which also contains $CH_4$ and Ar etc. The CO and $CO_2$ components must be removed before the feed gas enters the return circuit of the ammonia synthesis, to bring the level of impurities in the feed gas to ppm levels, otherwise the catalyst for the ammonia synthesis will be poisoned and deactivated. Generally, the purifying methods for the feed gas are the copper washing method, the deep hypo-transforming methanation method, the methanolizing and methanating method, and the liquid-nitrogen washing method. The copper washing method is technically developed, and widely used domestically, but it consumes copper, acetic acid, ammonia and a lot of steam. The liquid waste contains the heavy metal Cu, which contaminates the environment. The liquid-nitrogen washing method mainly applies to ammonia plants that use coke-oven gas as the feed gas. The purity of the processed feed gas is high, but an air-separating device is needed with it, and the range of use is limited. Regarding the deep hypo-transforming methanation method, the limit of sulfur content in the feed gas is critical, and the amount of steam used is large. Because the place of origin of coal and its sulfur content varies, this method is not applicable to medium- and small-sized chemical fertilizer plants, which take coal as the raw material.

Regarding the refining process for the feed gas, the replacement of the deep hypo-transforming methanation method or copper washing method with the fine desulfurization-methanolization-methanation method, with the byproduct of methanol, was firstly presented in Chinese patent No. ZL90105545.X, "Refinery Process for Feed Gas for Ammonia Synthesis" by Xie Ding-zhong etc of China Hunan Anchun High Tech Co., Ltd in September 1990. This process was formally put into operation in 1992. It runs very well and has distinct advantages, with a pressure range of only 5 to 15 MPa. Furthermore, it gives high purity, requires little material and energy consumption, and has wide applicability. Later, Haldor Topsoe of Denmark also suggested the adoption of the methanation process in an ammonia plant in 1991. A plant was built in Egypt in 1992, and planned to go into production in 1993. But the pressure of this method is 22 MPa, the moisture content in methanol is up to 40% to 50%, and external concurrent heating is needed to maintain the reaction. In Chinese patent No. ZL93105920.8, "Equal pressure device for the joint production of methanol and ammonia", it is presented that methanol synthesis and ammonia synthesis proceeded at the same high pressure. So the investment is large, the energy consumption is high, and the liquid nitrogen washing, copper washing or methanation methods are still needed for the refining of the feed gas.

The traditional methanation method above is used to make the purity of the feed gas meet the requirements of ammonia synthesis, and to avoid poisoning and deactivating the catalyst for ammonia synthesis. The content of CO and $CO_2$ in the feed gas can be refined to from 5 to 15 ppm. During the refining of the feed gas, the content of $CH_4$ will increase, but it won't take part in the ammonia synthesis reaction, and will accumulate gradually in the ammonia synthesis system and cause a pressure rise. When the pressure comes up to the safety control pressure, it is necessary to remove some gas mixture. When $CH_4$ is emptied, the effective gases in the gas mixture, such as $H_2$, $N_2$ and $NH_3$ etc, are lost at the same time. Therefore, the generation and entry of $CH_4$ should be avoided and decreased as much as possible during ammonia synthesis.

China is a country with rich coal resources and relatively insufficient oil. How to transfer rough solid mineral energy into relatively clean liquid fuel is also a problem to be solved urgently. However, there is no effective and economical ammonia synthesis technology to transfer most CO and $CO_2$ in the feed gas into high quality liquid fuels and multiple kinds of fine chemicals, and little into methane.

DESCRIPTION OF THE INVENTION

In the light of the above, the purpose of this invention is to present a kind of joint process for the production of an alcohol/ether mixture, an alcohol/hydrocarbon mixture, and synthetic ammonia. With this process, CO and $CO_2$ in the feed gas can be converted into liquid fuel and other fine chemicals efficiently, and with low loss, and the generated methane is relatively less. Through this process, an alcohol/ether mixture is firstly generated in the presence of a catalyst of the copper series for alcohol formation and etherification, and is separated by a water cooler. The residual CO and $CO_2$, accounting for 0.1% to 0.8%, then generate an alcohol/hydrocarbon mixture, catalysed by a catalyst of the iron series. After the mixture has been separated by a water cooler, the remaining $H_2$, $N_2$ and microquantities of CO and $CO_2$ are loaded into an ammonia synthesis system. During the hydrocarbon formation and formation of alcohol, CO and $CO_2$ generate an alcohol/hydrocarbon mixture, which can be separated by condensation, and used as a liquid fuel, so that the generation of $CH_4$ is decreased and thus the emptied amount is reduced during ammonia synthesis. Thereby, the consumption of the feed gas for ammonia synthesis is reduced, and the cost of production is cut down.

This invention is achieved through the following technical means. Two alcohol formation and etherification reactors loaded with a catalyst of the copper series are installed in the ammonia synthesis system, and the feed gas is pressurised to over 5.0 MPa. At a temperature of 210 to 280° C., most CO and $CO_2$ in the feed gas reacts with $H_2$ to form an alcohol/ether mixture, which is then condensed into a liquid after it has been cooled, and blown down into a storage tank for storage, after separation. After separation, the gas contains $H_2$, $N_2$ and 0.1% to 0.8% CO and $CO_2$, which generates an alcohol-/hydrocarbon mixture after entering the alcohol formation and hydrocarbon formation reactor, loaded with a catalyst of the iron series. Then, the alcohol-/hydrocarbon mixture is condensed into a liquid and blown down into another storage tank for storage, after gas-liquid separation and pressure relief. After separation, the gas contains $H_2$, $N_2$, $CH_4$ and no more than 10 ppm of CO and $CO_2$, and is delivered to the ammonia synthesis system to synthesize ammonia. The product is then condensed to yield liquid ammonia, and separated. The remains re-enter the synthesizing tower for reaction after the pressure and amount of feed gas have been compensated. The cycle is repeated continuously. All the reactors are joined up to one system through pipes, valves and circulators, to control the running.

EMBODIMENT

The structure and technical features of this invention are detailed as follows, in combination with the attached figures and examples of practice.

Figure 1:
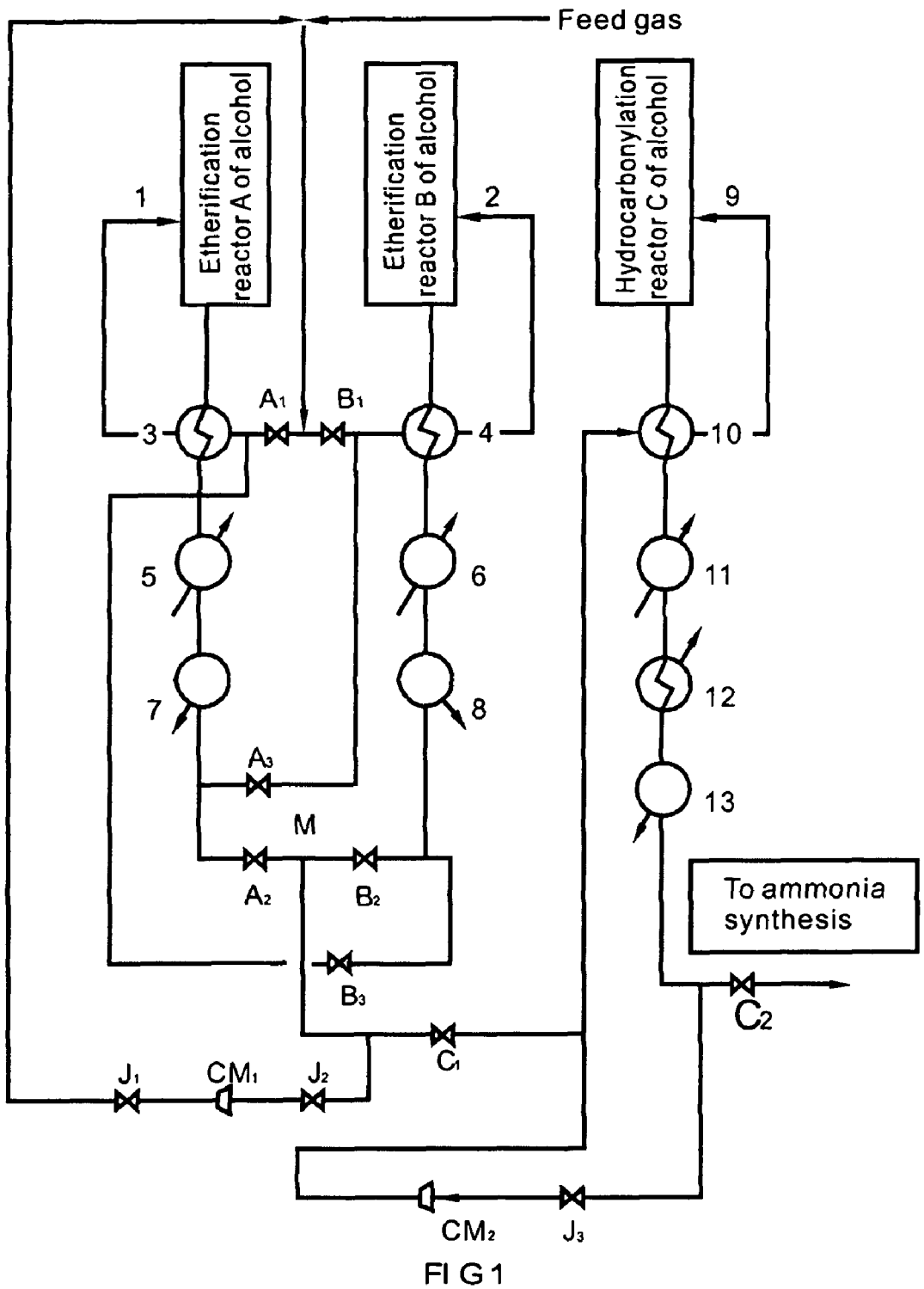
FIG. 1 is the process flow for this invention with CO≧1.8% in feed gas.

See FIG. 1. The whole system consists of: The alcohol formation and etherification reactor A (1), alcohol formation and etherification reactor B (2), alcohol formation and hydrocarbon formation reactor C (9), gas heat exchangers (3), (4) and (10), water coolers (5), (6) and (11), gas-liquid separators (7), (8) and (13), liquid ammonia cooler (12), two-way valves ($A_1$), ($A_2$), ($A_3$), ($B_1$), ($B_2$), ($B_3$), ($C_1$), ($C_2$), ($J_1$), ($J_2$) and ($J_3$), tee joint (M) and circulating machines ($CM_1$) and ($CM_2$). The alcohol formation and etherification reactor A (1) is connected to heat exchanger (3), water cooler (5) and gas-liquid separator (7) in series. The alcohol formation and etherification reactor B (2) is connected to heat exchanger (4), water cooler (6) and gas-liquid separator (8) in series. The alcohol formation and hydrocarbon formation reactor C (9) is connected to heat exchanger (10), water cooler (11), liquid ammonia cooler (12) and gas-liquid separator (13) in series. The system is connected with pipes, valves and circulating machines, and the flow direction is controlled with valves. The circulating machines are used for temperature rise and reduction of catalyst and temperature control during reaction. One of the main features of this invention is that two alcohol formation and etherification reactors, (1) and (2), are installed in the whole system. The feed gas contains $H_2$, $N_2$, CO and $CO_2$, with the content of $H_2$ and $N_2$ being 91% to 97%, and the content of CO and $CO_2$ being 1% to 8%. The total sulphur content will be decreased to below 1 ppm after the feed gas has been desulphurised, and then the feed gas is pressurised to over 5 MPa. With regard to the structural design of the products and the production run, there are several versions in demand, as follows.

1. If the proportion of ammonia to the alcohol/ether mixture is designed to be small, and the content of CO in the feed gas is high (more than 4% for example), parallel operation shall be adopted. The feed gas firstly enters the alcohol formation and etherification reactor loaded with a catalyst of the copper series, which mainly consists of Cu, Zn, Al and rare earth metals, to generate an alcohol/ether mixture. The process flow is that through main pipe, valves ($A_1$) and ($B_1$), heat exchangers (3) and (4), the feed gas is preheated to 210 to 220° C. and then enters the alcohol formation and etherification reactors (1) and (2). The alcohol/ether mixture is generated at 210 to 290° C. After reaction, the hot gas is cooled to 70 to 90° C. in a pipe through the heat exchangers (3) and (4). The alcohol and the ether in the gas are condensed to liquid through water coolers (5) and (6). The content of ether in the liquid is 30% to 40%. By means of separators (7) and (8), the separated liquid alcohol/ether mixture is discharged into the storage tank for storage. The gas converges at tee joint (M) through valves ($A_2$) and ($B_2$), and then enters the alcohol formation and hydrocarbon formation reactor (9) via valve ($C_1$).

The content of CO and $CO_2$ in the feed gas after alcohol formation and etherification is decreased to 0.1% to 0.8%. Via valve ($C_1$), the gas is preheated to 180 to 210° C. through heat exchanger (10), and then enters the alcohol formation and hydrocarbon formation reactor (9) loaded with a catalyst of the iron series, with the ingredients of Fe, Cu, Ni, K and Al etc., and generates alcohols, hydrocarbons and methane at 200 to 300° C. The mixture is cooled to 70 to 90° C. through heat exchanger (10), and then to 35 to 40° C. through water cooler (11). The alcohol/hydrocarbons mixture, and water vapour are condensed to liquid. Via ammonia cooler (12), the gas is continuously cooled to 5° C. to minimize the content of saturated vapour. The liquid alcohol, hydrocarbon and water mixture is separated out through separator (13). The alcohol/hydrocarbon mixture accounts for about 40% to 50% in the liquid. Now, the total content of CO and $CO_2$ in the gas has been decreased to below 10 ppm, meeting the requirements for ammonia synthesis. Then the gas is delivered to the ammonia synthesizing procedure.

CO and $CO_2$ in the feed gas mainly react with $H_2$ to generate the alcohol/ether mixture and the alcohol/hydrocarbon mixture. The chemical equations are as follows:

Alcohol Formation/Etherification:

$$CO+2H_2 \rightarrow CH_3OH$$

$$CO_2+3H_2 \rightarrow CH_3OH+H_2O$$

$$2CH_3OH \rightarrow (CH_3)_2O+H_2O$$

Hydrocarbon Formation/Alcohol Formation:

$$3H_2+CO \rightarrow CH_4+H_2O$$

$$4H_2+CO_2 \rightarrow CH_4+2H_2O$$

$$(2n+1)H+nCO \rightarrow CnH_{(2n+2)}+nH_2O$$

$$2nH_2+nCO \rightarrow CnH_{2n}+nH_2)$$

$$2nH_2+nCO \rightarrow CnH_{(2n+2)}O+(n-1)H_2O$$

The process flow above can be represented by the following simple arrow scheme.

Feed gas→valve ($A_1$) on→heat exchanger (3)→alcohol formation & etherification reactor A (1)→heat exchanger (in the pipe) (3)→water cooler (5)→gas-liquid separator (7)

Feed gas→valve ($B_1$) on→heat exchanger (4)→alcohol formation and etherification reactor B (2)→heat exchanger (in the pipe) (4)→water cooler (6)→gas-liquid separator (8)→valves ($A_2$) and ($B_2$) on→collect at tee joint (M)→valve ($C_1$) on→Alcohol formation and hydrocarbon formation system.

Brief introduction to the process flow for hydrocarbon formation/alcohol formation:

Gas after alcohol formation and etherification→valve ($C_1$) on→heat exchanger (10) preheating to 180° C. to 210° C.→alcohol formation and hydrocarbon formation reactor (9) generating alcohol, hydrocarbon and methane→heat exchanger (10) cooling to 70° C. to 90° C.→water cooler (11) cooling to 35° C. to 40° C., where the alcohol and hydrocarbon are condensed to liquid→liquid cooler (12) cooling to 5° C.→gas-liquid separator (13) separating out the liquid alcohol, hydrocarbon and water mixture. The liquid alcohol and hydrocarbon mixture accounts for about 40% to 50%. The content of CO and $CO_2$ in the gas is reduced to below 10 ppm.→-ammonia synthesis system When the catalyst in one of the alcohol formation and etherification reactors is in senescence phase, a serial process flow can be adopted as follows.

Feed gas→valve ($A_1$) on and valve ($B_1$) off→heat exchanger (3)→alcohol formation and etherification reactor A (1)→heat exchanger (3)→water cooler (5)→gas-liquid separator (7)→valve ($A_3$) on and valve ($A_2$) off→heat exchanger (4)→alcohol formation and etherification reactor B (2)→heat exchanger (4)→water cooler (6)→gas-liquid separator (8)→valve ($B_3$) off and valve ($B_2$) on→tee joint (M)→valve ($C_1$) on→alcohol formation and hydrocarbon formation system C (9).

2. If the proportion of ammonia to the alcohol/ether mixture is large during product design, that is, the content of CO in the feed gas is low (1.8 to 4% for example), then a single-tower system shall be adopted. The arrow flow diagram is as follows:

If reactor A (1) is used alone:
feed gas→valve ($A_1$) on and valve ($B_1$) off→heat exchanger (3)→alcohol formation and etherification reactor A (1)→heat exchanger (3)→water cooler (5)→gas-liquid separator (7), valves ($A_3$), ($B_2$) and ($B_3$) off and valve ($A_2$) on→tee joint (M)→vavle (C1) on→alcohol formation and hydrocarbon formation system (9).

If reactor B (2) is used alone:
Feed gas→valve ($A_1$) off and valve ($B_1$) on→heat exchanger (4)→alcohol formation and etherification reactor B (2)→heat exchanger (4)→water cooler (6)→gas-liquid separator (8), valves ($A_3$), ($A_2$) and ($B_3$) off and valve ($B_2$) on→tee joint (M)→valve ($C_1$) on→alcohol formation and hydrocarbon formation system (9).

Figure 2:
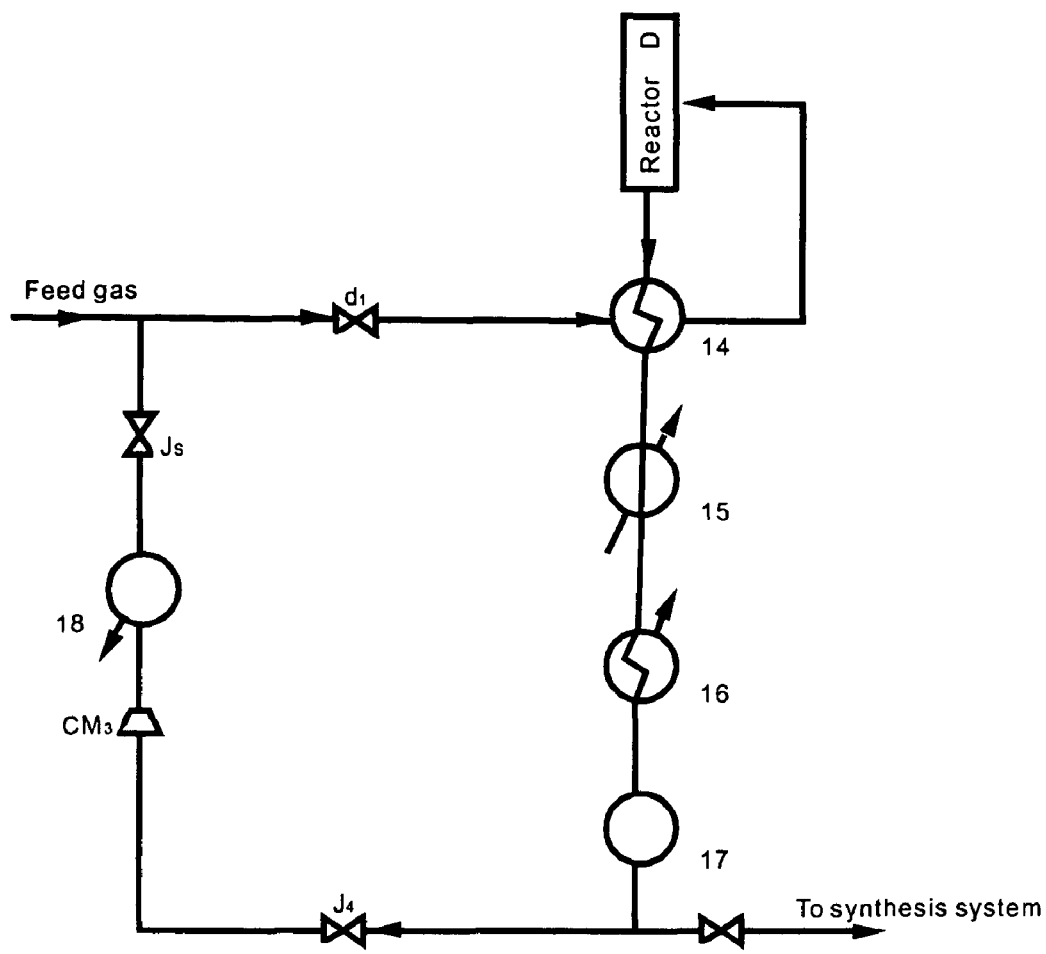
FIG. 2 is the process flow for this invention with CO≦1.8% in feed gas.

3. If the proportion of ammonia to alcohol/ether mixture is very large, that is, the content of CO in the feed gas is very low (below 1.8% for example), the alcohol formation and etherification and the alcohol formation and hydrocarbon formation take place in the same reactor, then the process flow and the equipment can be simplified. The upper part of the reactor is loaded with catalyst for formation of alcohol and etherification and the lower part is loaded with that for hydrocarbon formation and formation of alcohol. See FIG. 2 for the process flow.

Feed gas→valve ($d_1$) on and valve ($J_5$) off→heat exchanger (14)→reactor (D)→heat exchanger (14)→water cooler (15)→ammonia cooler (16)→separators (17) and valve ($J_4$) off→($d_2$) on→synthesizing system 4. There are two series of catalysts used in this invention.

The catalyst for the alcohol formation and etherification belongs to the copper series, and mainly consists of copper, zinc, aluminium and rare earth metals in an atomic ratio of Cu:Zn:Al=2 to 3:1:2 to 2.5, and $CeO_2$ at 3%. $Al_2O_3$ is active $Al_2O_3$. The outline dimensions of the catalyst are φ5×5 for a cylindrical catalyst and φ3~φ4 for a spherical catalyst, with a specific weight of 1.3 to 1.5 g/ml. The catalysed ratio of conversion of CO and $CO_2$ by the catalyst increases with increasing pressure, and the optimal reaction temperature is 210 to 290° C. The catalyst is in an oxidized state when leaving factory. It is activated and reduced to a metallic state with $H_2$ and $N_2$ after being loaded into the reactor.

The catalyst for the hydrocarbon formation and alcohol formation belongs to the iron series, and mainly consists of Fe, Al, K, Co and Ce, with the content of $Fe_3O_4$ being 80% to 85%, CaO 2% to 3.5%, $Al_2O_3$ 2.5% to 3.5%, $K_2O$ 0.8% to 2%, $CeO_2$ 0.5% to 2.5% and $Co_3O_4$ 3% to 4%. The catalyst in an oxidized state when leaving factory. It must be reduced to a metallic state to have activity after being loaded into the reactor. The catalyzed rate of conversion of CO and $CO_2$ by the catalyst increases with increasing pressure. The optimum reaction temperature is 200 to 300° C.

In order to control and adjust the content of ether, methanol [??] with an ether content of less than 0.5% can be produced by adjusting the proportion of copper in the catalyst for alcohol formation and etherification. On the other hand, an alcohol/ether mixture with an ether content of 5% to 30% can be obtained if the proportion of copper in the catalyst for alcohol formation and etherification is decreased, and that of $Al_2O_3$ is increased.

In order to control the reaction temperature and thermal reduction, a system circulating machine is designed in this invention for the thermal reduction of the catalyst in the reactors. The three reaction systems of the whole unit, two alcohol formation and etherification systems, and alcohol formation and hydrocarbon formation system, can be increased in temperature and reduced at the same time. During production, if the content of CO and $CO_2$ entering the system is too high, and the temperature rise is too fast, then the circulating machine can be started up to control the temperature. If the amount of CO and $CO_2$ entering the alcohol formation and hydrocarbon formation system is less than 0.4%, and the self-heating reaction cannot take place, external concurrent heating can be applied. If the electric heater in the reactor is used, the reacting gas can be heated outside to the lowest temperature needed for reaction with superheated steam or other high-temperature gas.

The process flow for thermal reduction is as follows:
Thermal reduction is conducted firstly for the alcohol formation and etherification system and lastly for the alcohol formation and hydrocarbon formation system.

a. Process flow for the thermal reduction of the two alcohol formation and etherification systems in parallel:
Turn on valves ($C_1$), ($A_3$) and ($B_3$), open two-way valves ($J_1$), ($J_2$), ($A_2$) and ($B_2$), switch on the circulating machine ($CM_1$), the reducing gas through two-way valve ($J_1$)→parallel operation and through valves ($A_1$) and ($B_1$)→entering alcohol formation and etherification reactor A (1) and alcohol formation and etherification reactor B (2)→respectively through valves ($A_2$) and ($B_2$)→converging at tee joint (M)→entering circulating machine ($CM_1$) via two-way valve ($J_2$). Repeat the cycle continuously till the temperature required.

b. One alcohol formation and etherification reactor is increased in temperature and reduced alone. Take reactor A (1) for example:
Turn off valves ($B_1$), ($B_2$) and ($B_3$)→turn on valves ($A_1$), ($A_2$) and ($J_2$), switch on circulating machine ($CM_1$) and two-way valve ($J_1$), the reducing gas through valves ($J_1$) and ($A_1$)→heat exchanger (3)→alcohol formation and etherification reactor A (1)→heat exchanger (3)→water cooler (5)→gas-liquid separator (7)→through valve ($A_2$), tee joint (M) and valve ($J_2$)→inlet of circulating machine ($CM_1$). Repeat the cycle above.

c. Temperature rise system for the alcohol formation and hydrocarbon formation system:
Turn off valves ($J_2$) and ($C_2$)→open valves ($C_1$) and ($J_3$) and switch on circulating machine ($CM_2$)→gas after alcohol formation from tee joint (M)→via valve ($C_1$) and heat exchanger (10)→alcohol formation and hydrocarbon formation reactor (9)→heat exchanger (10)→water cooler (11)→ammonia cooler (12)→gas-liquid separator (13)→valve ($J_3$), inlet of circulating machine ($CM_2$). Repeat the cycle above.

d. Temperature rise system for the alcohol formation and etherification and alcohol formation and hydrocarbon formation system in the same reactor:

When the catalyst for etherification and alcohol formation and that for hydrocarbon formation and alcohol formation is loaded into the same reactor, then the process flow for temperature rise (reduction) as follows:

Turn off valve ($d_2$), turn on valves ($J_4$) and ($J_5$) and switch on circulating machine ($CM_3$), feed gas→valve ($d_1$)→heat exchanger (14)→reactor (D)→heat exchanger (14)→water cooler (15)→ammonia cooler (16)→separator (17)→valve ($J_4$)→circulating machine ($CM_3$)→separator (18)→valve ($J_5$)→valve ($d_1$). Repeat the cycle above.

Another significant feature of this invention is that a wide range of pressures can be used, between 5 MPa to 40 MPa. Equal pressures or different pressures can be used for the alcohol formation and etherification reaction and the alcohol formation and hydrocarbon formation reaction. The higher the reaction pressure is, the faster the reaction rate, but the higher the energy consumption is, the more the equipment requires, and the larger the investment is. When the content of CO is high, and the yield of the alcohol/ether mixture is large, then the etherification and alcohol formation can take place at a relatively lower pressure, 5 to 15 MPa for example. But the pressure for the alcohol formation and hydrocarbon formation reaction can be equal to that for the ammonia synthesis, between 15 MPa and 40 MPa. On the other hand, if the content of CO in the feed gas is low, then the alcohol formation and etherification reaction and the alcohol formation and hydrocarbon formation reaction can take place at the same high pressure as that for ammonia synthesis, 10 to 40 MPa for instance.

The invention claimed is:

1. A process for preparing an alcohol/ether mixture, an alcohol/hydrocarbon mixture and synthesizing ammonia, said process comprising:
    i) pre-heating a feed gas to 210° C. to 220° C.: wherein the feed gas contains 91% to 97% $H_2$ and $N_2$. and 1% to 8% CO and $CO_2$, $CH_4$ and Ar;
    ii) performing desulfurization to lower the sulfur content in the feed gas to less than 1 ppm;
    iii) reacting the feed gas with a catalyst for alcohol formation and conducting etherification at 210° C. to 290° C. to form an alcohol/ether mixture;
    iv) cooling the mixture to 70° C. to 90° C.;
    v) condensing the mixture into liquid, wherein an ether content of 5% to 30% is obtained;
    vi) separating the alcohol/ether mixture from the reacted gas, wherein the CO and $CO_2$ content in the reacted gas is 0.1% to 0.8% after alcohol formation and etherification;
    vii) preheating the reacted gas having 0.1% to 0.8% CO and $CO_2$ content to 180° C. to 210° C.;
    viii) reacting the reacted gas with an iron catalyst to form an alcohol/hydrocarbon mixture and methane at a temperature of 200° C. to 300° C.;
    ix) cooling the alcohol/hydrocarbon mixture to 35° C. to 90° C.;
    x) condensing the alcohol/hydrocarbon mixture and water vapour into liquid;
    xi) cooling the liquid to 5° C.; and
    xii) separating the remaining gas and liquid from the alcohol, hydrocarbon and water mixture, wherein the remaining gas comprises $H_2$, $N_2$, methane, and not more than 10 ppm of CO and $CO_2$;
    xiii) synthesizing ammonia from the remaining gas and condensing the ammonia into liquid ammonia; separating and collecting the liquid ammonia; and optionally, collecting any finally remaining gas to supplement the feed gas in a repeated cycle of the process;
    wherein the catalyst for the step of alcohol formation and etherification is a catalyst of the copper series comprising copper, zinc, aluminum and rare earth metals in an atomic ratio of Cu:Zn:Al=2 to 3:1:2 to 2.5, $CeO_2$ at 3% and active $Al_2O_3$; and
    wherein the catalyst for the step of hydrocarbon formation and alcohol formation is a catalyst of the iron series, comprising 80% to 85% $Fe_3O_4$, 2% to 3.5% CaO, 0.8% to 2% $K_2O$, 2.5% to 3.5% $Al_2O_3$, 0.5% to 2.5% $CeO_2$ and 3% to 4% $Co_3O_4$.

2. The process according to claim 1, wherein alcohol formation and etherification are conducted in parallel or in series, and if the catalyst in an alcohol formation or etherification step is in a senescence phase, performing alcohol formation and etherification in series; wherein the content of CO in the feed gas is more than 4%.

3. The process according to claim 1, wherein the content of CO in the feed gas is 1.8% to 4%, a single formation step of alcohol and etherification is conducted, and a single formation step of hydrocarbon and an alcohol is conducted.

4. The process according to claim 1, wherein the content of CO in the feed gas is less than 1.8%, the step of alcohol formation and etherification and the step of hydrocarbon formation and alcohol formation are conducted together.

5. The process according to claim 4, wherein the step of alcohol formation and etherification and the step of hydrocarbon formation and alcohol formation are conducted in a reactor wherein the catalyst for formation of alcohol and etherification is added at one end of the reactor and the catalyst for hydrocarbon formation and formation of alcohol is added at another end of the reactor.

6. The process according to claim 1, wherein the catalyst is activated and reduced to a metallic state by $H_2$ and $N_2$.

7. The process according to claim 2, wherein a reaction pressure is from 5 to 40 Mpa and the reaction pressure for the steps of etherification and hydrocarbonylation of alcohol are the same or different.

8. The process according to claim 3, wherein the catalyst is activated and reduced to a metallic state by $H_2$ and $N_2$.

9. The process according to claim 4, wherein the catalyst is activated and reduced to a metallic state by $H_2$ and $N_2$.

10. The process according to claim 5, wherein the catalyst is activated and reduced to a metallic state by $H_2$ and $N_2$.

* * * * *